United States Patent [19]

Mark et al.

[11] 4,277,600

[45] Jul. 7, 1981

[54] TETRAPHENOLIC COMPOUNDS AND POLYCARBONATES CONTAINING THE SAME

[75] Inventors: Victor Mark, Evansville; Charles V. Hedges, Mt. Vernon, both of Ind.

[73] Assignee: General Electric Company, Mt. Vernon, Ind.

[21] Appl. No.: 76,973

[22] Filed: Sep. 20, 1979

[51] Int. Cl.$^3$ .................. C08G 63/62; C07C 39/15
[52] U.S. Cl. .................................. 528/204; 568/719; 568/720
[58] Field of Search ............... 528/204; 568/719, 720

[56] References Cited

U.S. PATENT DOCUMENTS

| 2,964,797 | 12/1960 | Peilstocker et al. | 528/204 |
| 3,062,780 | 11/1962 | Rinke et al. | 528/204 |
| 3,644,538 | 2/1972 | Starnes | 568/720 |
| 4,009,148 | 2/1977 | Neuray et al. | 528/204 |

FOREIGN PATENT DOCUMENTS

2804215 2/1979 Fed. Rep. of Germany ........... 568/720

*Primary Examiner*—Natalie Trousof
*Assistant Examiner*—Vera C. Clarke
*Attorney, Agent, or Firm*—Martin B. Barancik; William F. Mufatti

[57] ABSTRACT

Novel tetraphenolic compounds are disclosed. These compounds have utility as branching agents in the production of novel, randomly branched polycarbonates.

9 Claims, No Drawings

TETRAPHENOLIC COMPOUNDS AND POLYCARBONATES CONTAINING THE SAME

This invention relates to novel tetraphenolic compounds that have utility as branching agents and thermoplastic, randomly branched polycarbonates produced therefrom having excellent resistance to thermal oxidation and excellent blow molding properties and to a process for their preparation.

BACKGROUND OF THE INVENTION

Polycarbonates are well known, commercially important materials which are produced in large quantities. Such polymers are typically prepared by reacting a carbonate precursor with a dihydric phenol to provide a linear polymer consisting of units of the dihydric phenol linked to one another through carbonate linkages. These polymers have outstanding mechanical, thermal, and optical properties such as high tensile strength, optical clarity (transparency), thermal and dimensional stability and impact strength.

These aromatic polycarbonates differ from most thermoplastic polymers in their melt rheology behavior. Most thermoplastic polymers exhibit non-Newtonian flow characteristics over essentially all melt processing conditions. Newtonian flow is defined as the type of flow occurring in a liquid system where the rate of shear is directly proportional to the shearing force. However, in contrast to most thermoplastic polymers, polycarbonates prepared from dihydric phenols exhibit Newtonian flow at normal processing temperatures and shear rates below 300 reciprocal seconds.

Two other characteristics of molten thermoplastic polymers are considered to be significant for molding operations: melt elasticity and melt strength. Melt elasticity is the recovery of the elastic energy stored within the melt from distortion or orientation of the molecules by shearing stresses. Melt strength may be simply described as the tenacity of a molten strand and indicates the ability of the melt to support a stress. Both of these characteristics are important in extrusion blow molding, particularly in fabrication by extrusion blow molding. Non-Newtonian flow characteristics tend to impart melt elasticity and melt strength to polymers thus allowing their use in blow molding fabrication. In the usual blow molding operation, a tube of a molten thermoplastic is extruded vertically downward into a mold, followed by the introduction of a gas, such as air, into the tube thus forcing the molten plastic to conform to the shape of the mold. The length of the tube and the quantity of material forming the tube are limiting factors in determining the size and wall thickness of the objects that can be molded by this process. The fluidity of the melt obtained from bisphenol-A polycarbonate, or the lack of melt strength as well as the paucity of extrudate swelling, serve to limit blow molding applications to relatively small, thin walled parts. Temperatures must generally be carefully controlled to prevent the extruded tube from falling away before it attains the desired length and the mold is closed around it for blowing. Consequently, the Newtonian behavior of polycarbonate resin melts has severely restricted their use in the production of large hollow bodies by conventional extrusion blow molding operations as well as the production of various other shapes by profile extrusion methods.

Thermoplastic randomly branched polycarbonates exhibit unique properties of non-Newtonian flow, melt elasticity and melt strength which permit them to be used to obtain such articles as bottles which were not heretofore easily or readily produced with linear polycarbonates. The thermoplastic, randomly branched polycarbonates can be prepared by reacting a polyfunctional compound containing three or more functional groups with a dihydric phenol and a carbonate precursor.

DESCRIPTION OF THE INVENTION

The novel compounds of the invention are tetraphenolic compounds of the formula I:

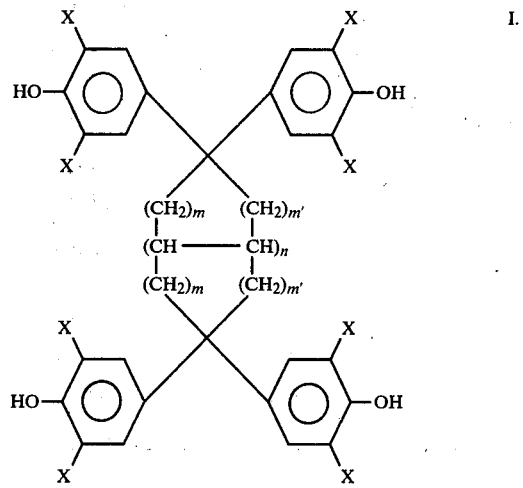

wherein each X substituent is independently selected from phenyl, H, Cl, Br, and $C_1$-$C_5$ alkyl; each m and m' are integers which are independently selected from 0, 1, 2 and 3; and n is an integer of either 0 or 1, with the proviso that the sum of all the m and m' integers and n is at least 2, and with the further proviso that at least one of the m integers is greater than 0 and at least one of the m' integers is greater than 0.

In the specification and claims, the terms $C_1$-$C_5$ represent radicals having from 1 to 5 carbon atoms. The term "alkyl" is used herein to represent both straight and branched chain alkyl groups.

The invention's novel tetraphenolic compounds are crystalline solids which are of low solubility in water and of moderate solubility in many organic solvents, but fair to good solubility in lower alcohols and dipolar, aprotic solvents. These compounds have been found to have utility as excellent branching agents in the production of randomly branched aromatic polycarbonates when copolymerized with dihydric phenols is simple, one-step processes.

This invention is also directed to novel thermoplastic randomly branched aromatic polycarbonate compositions based on a dihydric phenol and having an I.V. of 0.40 to 1.00 dl/g in methylene chloride at 25° C., wherein the branching component is a compound of formula I above. These novel polycarbonate compositions have excellent blow molding properties and are prepared by reacting a carbonate precursor, a dihydric phenol, and a compound of formula I above.

These novel tetraphenolic compounds are obtained from the corresponding dione precursors and monofunctional phenols under either acidic or alkaline condensing conditions, as shown by the following generalized equation and as illustrated by the detailed procedures described in the examples:

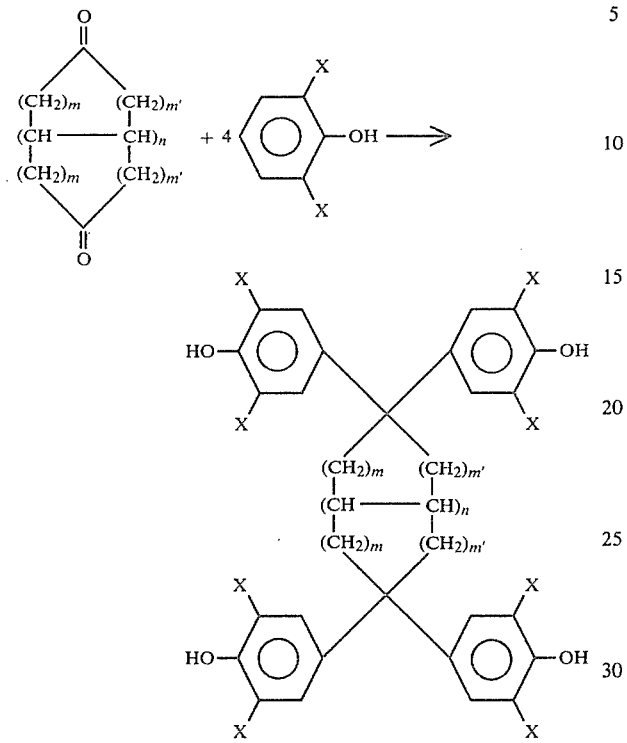

wherein the symbols X, m, m' and n are as set forth above.

In the above reaction a diphenol intermediate is formed which converts to the desired tertraphenolic compound. This diphenol intermediate has the formula:

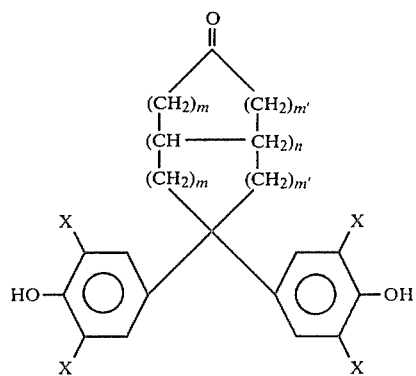

wherein m, m', n and X are as defined above.

In this reaction the molar ratio of the phenol to dione starting materials should be at least 4:1. Molar ratios significantly above 4:1, such as, for example, 10:1, may be utilized without deleterious side effects, since the excess phenol also functions as a reaction solvent. When the reaction is carried out under acidic conditions, a catalyst containing the sulfhydryl (—SH) function may be employed. Examples of the sulfhydryl catalysts are ethanethiol, 1-butanethiol, thiophenol and mercaptoacetic acid.

The condensation reaction is best carried out by utilizing the phenolic reactant in excess of the stoichiometric amount. With phenols that are solid at ambient temperature, this method requires reaction temperatures near or above the melting point of the phenol that is used in excess. In addition, non-phenolic solvents, such as acetic acid, acetic anhydride, methylene chloride, can be used.

The reaction temperature encompasses ambient temperatures to elevated temperatures, such as 100° C. or higher. Although the reaction rate is faster at higher temperatures, there is also an increase in undesired by-products, such as isomeric tetraphenols, which are less effective than the entirely p-substituted tetraphenols in the copolymerization reaction with the diphenols.

The condensation reaction can be carried out either at atmospheric or superatmospheric pressures.

The progress of the condensation reaction can be monitored by chromatographic or spectroscopic methods. Since the reaction takes place stepwise, it becomes relatively easy to follow the production of the intermediate diphenol carbonyl compound. It is understood that this intermediate compound may be isolated and later utilized to form the desired tetraphenol compound. If the intermediate diphenol is left in the reaction mixture it will convert to the desired tetraphenolic compound.

The reaction can be followed readily by infrared (ir) spectroscopy by the diminution or disappearance of the carbonyl band, a very strong, characteristic and diagnostic ir band, well suitable for qualitative and quantitative analysis.

Similarly, proton nuclear magnetic resonance spectroscopy can sometimes be used at great advantage: an increase of resonance peaks in the aromatic region that are characteristic of the product, and not the precursor, can yield a readily available, quantitative information via integration of the specific aromatic and aliphatic region signals.

When X represents chlorine or bromine substituents, the novel tetraphenols can also be prepared by direct halogenation, in solution or suspension, of the corresponding novel non-halogenated tetraphenols. Methylene chloride, chloroform, acetic acid, water, other non-reactive liquids and aqueous sodium hydroxide solution may be used as solvents or dispersants. The degree of halogenation can readily be followed by gas or liquid chromatography, ir or proton nmr.

The phenolic moieties on the invention's novel compounds may be similarly substituted or they may be "mixed," i.e., one or more of these moieties may have different substituents. One particularly convenient method of preparing mixed tetraphenolic compounds of the present invention is to react a dione precursor with a phenol starting material as set forth above, isolate the intermediate diphenol, and react this diphenol with a different phenol compound to thereby form a mixed tetraphenol compound.

Purification of the novel tetraphenolic compounds can be carried out by recrystallization, elution chromatography, or other methods known to those skilled in the art. Preferred solvents of recrystallization are methylene chloride, benzene, cyclohexane, methanol, ethanol and alcohol-water mixtures. Elution chromatography is carried out best over alumina or silica, using a variety of solvents as eluants.

The new tetraphenolic compounds can be used for the preparation of branched polycarbonates. Another subject of the instant invention is, therefore, the novel, high molecular weight, branched polycarbonates which are substantially free of crosslinking.

In the preparation of the novel thermoplastic randomly branched polycarbonates of this invention, the amount of the tetraphenolic compound which is reacted with the dihydric phenol and the carbonate precursor is critical to the extent that the amount employed must be sufficient to produce a true thermoplastic randomly branched polycarbonate which is substantially free of crosslinking. If an amount of tetraphenolic compound employed is less than about 0.01 mole percent, based upon the moles of the dihydric phenol employed, the resulting polymer will not exhibit the degree of non-Newtonian melt characteristics desired for blow molding and/or melt extrusion purposes. Preferably, it is desirable to employ 0.01 to about 3.0 and more particulaly, 0.01–1.0 mole percent of the tetraphenolic compound, based upon the total moles of dihydric phenol.

The dihydric phenols that can be employed in the practice of this invention include bis(4-hydroxyphenyl)methane, 1,1-bis(4-hydroxyphenyl)ethane, 2,2-bis(4-hydroxyphenyl)propane, also called bisphenol-A or BPA, 2,2-bis(4-hydroxy-3-methylphenyl)propane, 3,3-bis(4-hydroxyphenyl)pentane, 2,2-bis(4-hydroxy-3-chlorophenyl) propane, 2,2-bis(4-hydroxy-3,5-dibromophenyl)propane, 1,1-bis (4-hydroxyphenyl)cyclohexane, p,p'-dihydroxydiphenyl, 3,3'-dichloro-4,4'-dihydroxydiphenyl, bis(4-hydroxyphenyl)ether, bis(4-hydroxyphenyl)sulfone, bis(3,5-dimethyl-4-hydroxyphenyl)sulfone, resorcinol, hydroquinone; 1,4-hydroxy-2,5-dichlorobenzene, 1,4-dihydroxy-3-methylbenzene, bis(4-hydroxyphenyl)sulfoxide, bis(3,5-dimethyl-4-hydroxyphenyl)sulfoxide, and the like. A variety of additional dihydric phenols can also be employed such as are disclosed in U.S. Pat. Nos. 2,999,835, 3,028,365 and 3,153,008. It is, of course, possible to employ two or more different dihydric phenols or a copolymer of a dihydric phenol with glycol or with hydroxy or acid terminated polyester, or with a dibasic acid in the event a polycarbonate copolymer or interpolymer (copolyestercarbonate) rather than a homopolymer is desired for use in the preparation of the branched polymers of this invention. The preferred dihydric phenol is bisphenol-A.

The carbonate precursor employed can be either a carbonyl halide, a haloformate or a diaryl carbonate. Thus the carbonyl halides can be carbonyl chloride, carbonyl bromide, and mixtures thereof. The haloformates suitable for use include mono- or bishaloformates of dihydric phenols (bischloroformates of hydroquinone, monochloroformate of bisphenol-A, etc.) or bishaloformates of glycols (bishaloformates of ethylene glycol, neopentyl glycol, polyethylene glycol, etc.). When using bishaloformates, equimolar amounts of free dihydric phenols are required to effect polymerization. When polymerizing monohaloformates of diphenols no free diphenol is required. While other carbonate precursors will occur to those skilled in the art, carbonyl chloride, also known as phosgene, is preferred.

The polymerization of dihydric phenols to high molecular weight polycarbonates may be carried out by any conventional method known in the art. For example, phosgene can be introduced into a solution of the diphenol in organic bases, such as pyridine, triethylamine, dimethylaniline or into solutions of the diphenol in suitable organic solvents, such as benzene, toluene, chlorobenzene, methylene chloride, carbon tetrachloride and the like, with the addition of acid binding agents.

In the most widely practiced polymerization process phosgene is introduced into an aqueous solution of the alkali metal salt of the diphenol in the presence of methylene chloride and a phase-transfer catalyst as well as a molecular weight regulator, usually a monofunctional phenol. One advantage of the instant invention is that the tetraphenolic branching agent has the same reactivity profile as the diphenol used to make the linear chains, hence it can be added, in the desired amount, together with the diphenol at the beginning of the polymerization process. In other words, the tetraphenolic compounds can be formulated directly into the reaction mixture to be polymerized to branched polycarbonates.

The reaction between the halogen containing carbonate precursor and the dihydric phenol and the tetraphenolic branching agent when carried out by the interfacial method in accordance with this invention is conducted in the presence of an inert organic solvent which is essentially immiscible with water and does not deleteriously affect the formed polymer. Examples of suitable organic solvents are methylene chloride, ethylene dichloride and chlorobenzene.

In a preferred variant of the polymerization process, the branching tetraphenol is added in the form of an aqueous solution of its alkali metal salt. This is possible since the novel tetraphenols of the instant invention are capable of forming stable aqueous solutions in the form of their alkali salts. The novel branching agent may also be formulated into the reaction mixture of the dihydric phenol to be polymerized in finely divided solid form or as a methylene chloride solution or slurry. In either form it is copolymerized readily in the polycarbonate forming process and becomes a fully incorporated segment of the polymer system.

The alkali metal hydroxide which can be employed in the polymerization process can be any of the alkali metal hydroxides selected from the groups consisting of the alkali group and alkaline earth groups. Specifically, these include potassium hydroxide, sodium hydroxide, lithium hydroxide, calcium hydroxide, magnesium hydroxide and the like.

The interfacial, or phase-transfer catalysts, which can be employed in the polymerization process can be any of the suitable catalysts that aid the polymerization of dihydric phenols with phosgene. Suitable catalysts include tertiary amines such as triethylamine, tripropylamine, N,N-dimethylaniline and the like; quaternary ammonium compounds such as tetraethylammonium chloride, cetyl triethyl ammonium bromide, tetra-n-heptylammonium iodide, tetra-n-propyl ammonium chloride, tetramethylammonium chloride, tetramethylammonium hydroxide, tetra-n-butylammonium iodide, benzyltrimethylammonium chloride and the like; and quaternary phosphonium compounds such as n-butyltriphenyl phosphonium bromide and tetrabutyl phosphonium chloride and the like.

The molecular weight regulators which can be employed in the interfacial process include monohydric phenols such as phenol, chroman-I [4-(2,4,4-trimethylchromanyl)phenol], p-t-butyl phenol, p-cumyl phenol, primary and secondary amines, and the like. Preferably, phenol is employed as the molecular weight regulator.

It is sometimes desirable to introduce reducing agents, such as sodium dithionite into the aqueous system in order to supress the formation of colored contaminants.

The aqueous interfacial polymerization method may be carried out at temperatures from ambient to about 50° C. However, higher temperatures are within the scope of this invention since the instant method is not temperature dependent.

The diphenol-tetraphenol mixture can be converted into branched polycarbonates also by esterification with dialkyl, alkylaryl or diaryl carbonates at elevated temperatures from about 50° C. to about 325° C., at atmospheric or at reduced pressure, in neat form, or in the presence of neutral diluents or in the presence of transesterification catalysts, such as metal oxides, hydroxides, carbonates and the like, as known in the art. When using aryl carbonates, phenols are generated in the transesterification process, so that no molecular weight regulators need be added to the reaction mixture. In fact, the degree of polymerization is controlled by the extent of removal of the monohydroxylic coproducts, such as alcohols or phenols.

The branched polycarbonates, when produced according to the instant invention by the interfacial polymerization technique, were recovered from the washed, neutral methylene chloride phase by steam precipitation and drying and were fed into an extruder operating at 265° C. and the extrudates were comminuted into pellets. When prepared by the transesterification method, the polycarbonate melt was directly converted into extrudate and pellets.

While some of the physical-mechanical measurements can be carried out directly with the polycarbonate powder or pellets, some tests require molded specimens. To provide these, the pellets are injection molded at about 315° C. into test bars according to the dimensions required by the test method, such as the notched Izod impact test carried out according to ASTM D-256.

The following test procedures were utilized:

Intrinsic viscosity (I.V.) was determined in methylene chloride solution at 25° C. and is given as deciliters per gram (dl/g).

Molecular weight determinations (number average, $M_n$; weight average, $M_w$ and Z-average, $M_z$) were carried out on Waters Associates GPC Model 200, in methylene chloride solution.

Modified melt flow (K.I.) values, expressed in centiseconds, were obtained by an automated ASTM D-1238 procedure at 300° C. on a Tinius Olsen Melt Indexer, Model T-3, Condition 0.

Melt index ratio (M.I.R.), which is the ratio of melt flow rates at two different shear levels, and is a measure of the non-Newtonian property of the polymer, was obtained on the Tinius Olsen Melt Indexer described above. The M.I.R. values of linear Newtonian polycarbonates are typically less than 1.4, while those of the branched polycarbonates are typically higher than 1.5.

The branched polycarbonates produced according to the instant invention are soluble in selected organic solvents and can be worked into shaped articles from solutions, such as into films. Being thermoplastic, these branched polycarbonates can be easily fabricated by conventional shaping methods from melt, such as by extrusion, molding, blow-molding, lamination and the like.

It is also regarded to be among the features of this invention to include in the composition other ingredients such as fillers, mold release agents, pigments, dyestuffs, stabilizers and the like, in conventional amounts for their conventionally employed purposes.

DESCRIPTION OF THE PREFERRED EMBODIMENT

The following examples are set forth to illustrate the invention and are not to be construed to limit the scope of the invention. The product tetraphenolic compounds are identified by ir and nmr. In the following examples all the tetraphenolic compounds were produced in greater than 90% yield.

EXAMPLE 1

Preparation of the tetraphenol: 1,1,4,4-tetra-bis(4-hydroxyphenyl)cyclohexane

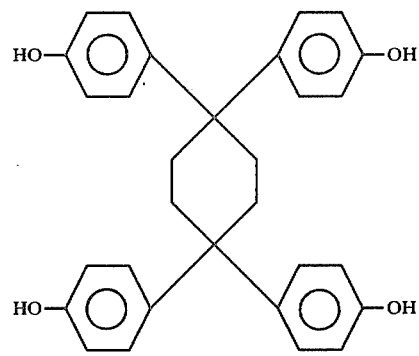

Into a molten mixture of 300 g (3.2 mole) of phenol and 22.42 g (0.2 mole) of 1,4-cyclohexanedione (m.p. 77.0°–78.5° C.), there was introduced hydrochloric acid gas at 50° C. until saturation was obtained. The resulting reaction mixture, that acquired a red color, was kept at 50° C. until the separation of white solids was complete. The intermediate diphenol, of the following structure

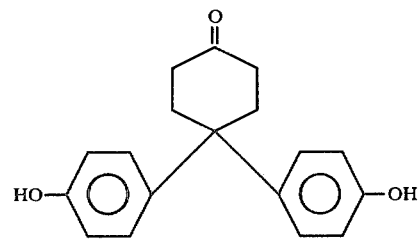

was quantitatively converted into the title tetraphenol, as determined by gas chromatography. The precipitate was filtered off through a sintered glass funnel and the filtercake rinsed with methylene chloride until phenol-free. The colorless crystalline tetraphenol was 99.3% pure by gas chromatographic analysis and had a melting point of 328°–329° C. Ir and nmr spectra were consistant with the structure shown above. Stripping of the phenolic mother liquor and the methylene chloride washing yielded more of the above tetraphenol contaminated to a small extent with 1-(2-hydroxyphenyl)-1,4,4-tris(4-hydroxyphenyl)cyclohexane.

EXAMPLE 2

Preparation of a polycarbonate branched with 1,1,4,4-tetrakis(4-hydroxyphenyl)cyclohexane To a well stirred mixture of 2283 g (10 moles) of 2,2-bis(4-hydroxyphenyl)propane, (BPA), 7000 ml of methylene chloride, 5500 ml of water, 31.1 g (0.33 mole) of phenol, 20.2 g (0.2 mole) of triethylamine and enough 45% aqueous sodium hydroxide solution to maintain a pH of 11.5, there was added a clear, colorless solution of 9.05 g (0.020 mole) of 1,1,4,4-tetrakis(4-hydroxyphenyl)cyclohexane, prepared in accordance with Example 1, in 30% aqueous sodium hydroxide. The introduction of phosgene into the well stirred reaction mixture was carried out at a rate of 30 g/minute for 47 minutes, continuously adjusting the pH to remain between 11.1 and 11.8, until the BPA content of the aqueous phase was reduced to 8 parts per million.

The recovered branched polycarbonate from the washed, neutral methylene chloride phase by steam precipitation and drying had the following properties: I.V. 0.619 dl/g; $M_n$ 18,300; $M_w$ 40,500; $M_z$ 71,800; K.I. 16,800 csec.; M.I.R. 2.34 and notched Izod impact 16.0 ft.lb.

EXAMPLE 3

Preparation of the tetraphenol: 1,1,4,4-tetrakis(4-hydroxy-3,5-dimethyl)cyclohexane

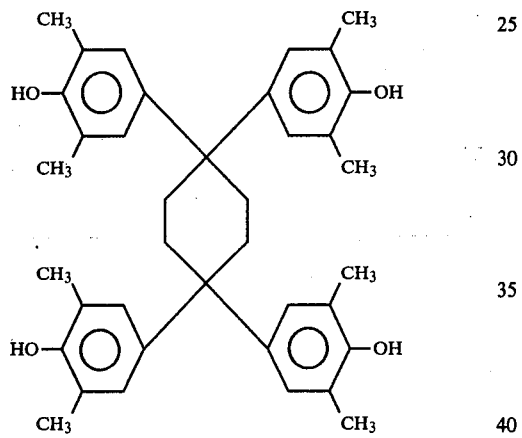

The procedure of Example 1 was repeated, except that 400 g of 2,6-xylenol was substituted for phenol and 1 ml of 1-butanethiol cocatalyst was also added. After the reaction was complete, as determined by gas chromatography (gc) analysis, the crystalline precipitate was filtered off and washed xylenol-free with methylene chloride. The novel white, crystalline tetraphenol was found to be 100% pure by gc and had a melting point of 332°–334° C. Ir and nmr spectroscopy confirmed the tetraphenol structure shown above.

EXAMPLE 4

Preparation of a branched polycarbonate with the tetraphenol of Example 3

The procedure of Example 2 was exactly repeated except that the tetraphenol described in Example 1 was replaced with 11.3 g (0.020 mole) of 1,1,4,4-tetrakis(4-hydroxy-3,5-dimethyl)cyclohexane of Example 3, in the form of its aqueous sodium hydroxide solution and the phosgenation was carried out between pH 12 and 13. The branched polymer, recovered by steam precipitation, had the following characteristics: I.V. 0.578; $M_n$ 16,600; $M_w$ 35,100; $M_z$ 65,000; K.I. 13,100; M.I.R. 2.23 and notched Izod impact 15.9 ft.lb.

EXAMPLE 5

Preparation of the tetraphenol: 3,3,7,7-tetrakis(4-hydroxyphenyl)bicyclo[3.3.0]octane

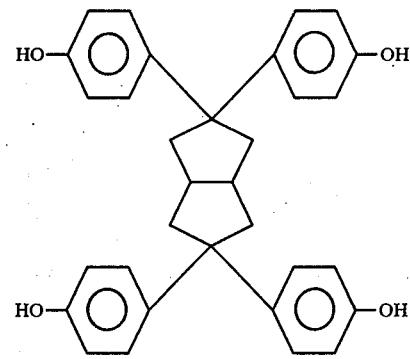

The procedure of Example 1 was repeated, except that cyclohexanedione was replaced with 27.6 g (0.2 mole) of bicyclo[3.3.0]octane-3,7-dione (m.p. 84°–86° C.). When the separation of the crystalline precipitate was complete and the intermediate diphenol

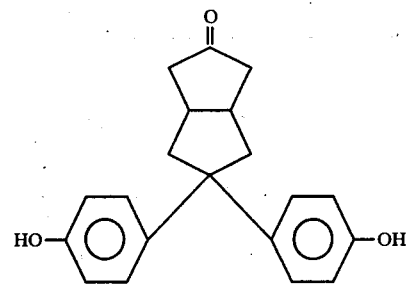

was quantitatively converted into the tetraphenol, the reaction mixture was filtered and the crystalline tetraphenol was washed with methylene chloride. Recrystallization from methanol-water yielded colorless crystals, that melted at 318°–319° C. and were 96.1% pure by gc.

EXAMPLE 6

Preparation of a branched polycarbonate with the tetraphenol of Example 5.

The procedure of Example 2 was exactly repeated except that the tetraphenol of Example 1 was replaced with an aqueous solution of the sodium salt of 3,3,7,7-tetrakis(4-hydroxyphenyl)bicyclo[3.3.0]octane (9.57 g, 0.02 mole). The branched polycarbonate had the following properties: I.V. 0.596; K.I. 16,300; $M_n$ 17,200; $M_w$ 43,100; $M_z$ 79,900; M.I.R. 2.82 and notched Izod impact of 16.1 ft. lb.

EXAMPLE 7

Preparation of the tetraphenol: 3,3,7,7-tetrakis(4-hydroxy-3-methylphenyl)bicyclo[3.3.0]octane

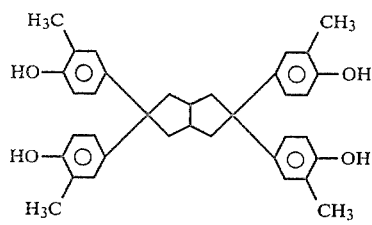

The procedure of Example 5 was repeated except that phenol was replaced with o-cresol. The progress of the reaction was monitored by gc. When the conversion of the intermediate diphenolketone into the tetraphenol was complete, the excess cresol was stripped off by distillation at water aspirator vacuum and the solid residue was recrystallized from aqueous methanol. The tetraphenol was 98.8% pure by gc and had a melting point of 280°–281° C.

EXAMPLE 8

Preparation of a branched copolycarbonate from 2,2-bis(4-hydroxy-3-chlorophenyl)propane and BPA with the tetraphenol of Example 7

The procedure illustrated in Example 2 was exactly repeated, except that BPA was replaced with a mixture of 2054.5 g (9 moles) of BPA and 297.2 g (1.0 mole) of 2,2-bis(4-hydroxy-3-chlorophenyl)propane and the tetraphenol was replaced with 10.70 g (0.020 mole) of 3,3,7,7,-tetrakis(4-hydroxy-3-methylphenyl)bicyclo[3.3.0]octane. The novel, branched copolycarbonate had the following properties: I.V. 0.606; K.I. 18,880; M.I.R. 2.82 and notched Izod of 14.8 ft. lb.

Structurally depicted below are additional examples of novel tetraphenols which can be prepared by the procedures as generally set forth herein:

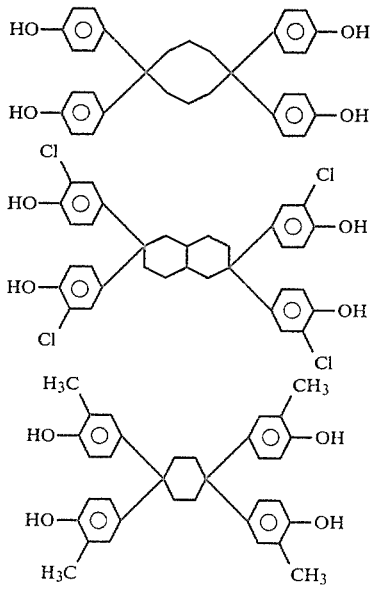

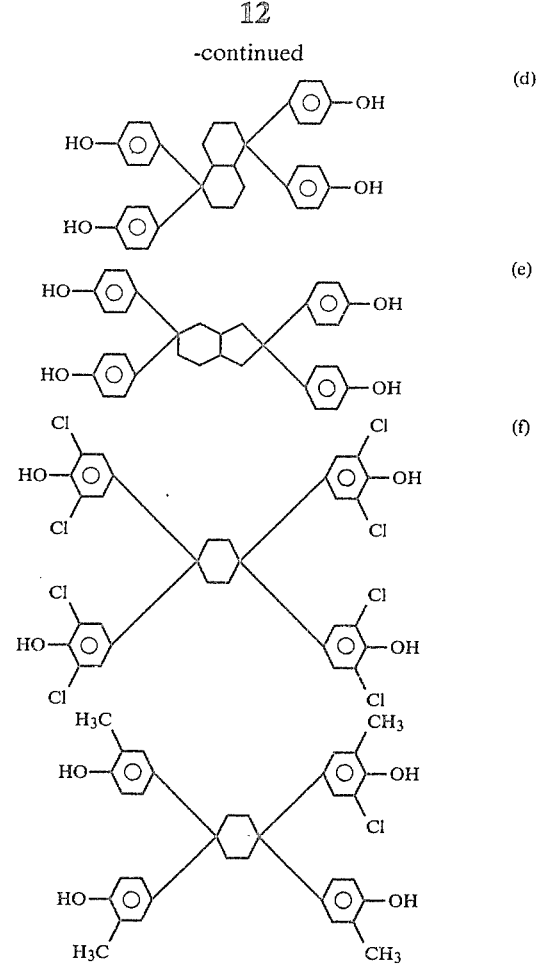

What is claimed is:

1. A tetraphenolic compound of the formula

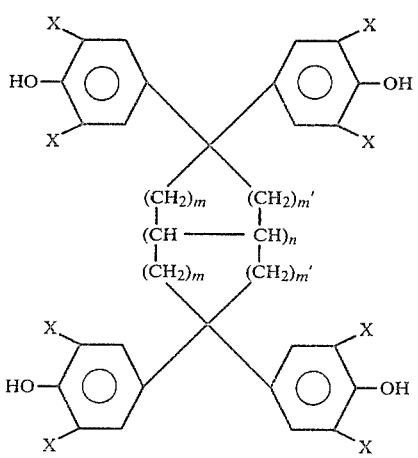

wherein each X substituent is independently selected from phenyl, H, Cl, Br, and $C_1$ to $C_5$ alkyl; each m and m' are integers selected independently from 0, 1, 2 and 3; and n is an integer of either 0 or 1, with the proviso that the sum of all the m and m' integers and n is at least 2, and with the further proviso that at least one of the m integers is greater than 0 and at least one of the m' integers is greater than 0.

2. The compound 1,1,4,4-tetrakis(4-hydroxyphenyl)cyclohexane.

3. The compound 1,1,4,4-tetrakis(4-hydroxy-3-methylphenyl)cyclohexane.

4. The compound 1,1,4,4-tetrakis(4-hydroxy-3,5-dimethylphenyl)cyclohexane.

5. The compound 3,3,7,7-tetrakis(4-hydroxyphenyl)-bicyclo[3.3.0]octane.

6. The compound 4,4-bis(4-hydroxyphenyl)cyclohexanone.

7. A high molecular weight, thermoplastic, randomly branched polycarbonate composition, said polycarbonate substantially free of crosslinking, based on a dihydric phenol, having an intrinsic viscosity of 0.40 to 1.00 dl/g in methylene chloride at 25° C., wherein the branching component is a compound of claim 1.

8. The composition of claim 7 wherein the branching component is 1,1,4,4-tetrakis(4-hydroxyphenyl)cyclohexane.

9. The composition of claim 7 wherein the branching component is 1,1,4,4-tetrakis(4-hydroxy-3-methylphenyl)cyclohexane.

* * * * *